United States Patent [19]
Bengsch et al.

[11] Patent Number: 6,133,198
[45] Date of Patent: Oct. 17, 2000

[54] METHOD OF TREATING VIROID INFECTIONS WITH BIOASSIMILABLE BORON COMPOUNDS

[75] Inventors: Eberhard Bengsch, Munich; Antonius Kettrup, Amsberg; Jürgen Polster, Freising, all of Germany

[73] Assignee: GSF Forschungszentrum für Umwelt und Gesundheit GmbH, Oberschleissheim, Germany

[21] Appl. No.: 09/215,764

[22] Filed: Dec. 19, 1998

Related U.S. Application Data

[60] Division of application No. 08/859,733, May 21, 1997, abandoned, which is a continuation-in-part of application No. PCT/EP95/04494, Nov. 15, 1995.

[30] Foreign Application Priority Data

Nov. 22, 1994 [DE] Germany .............................. 44 41 483

[51] Int. Cl.⁷ ...................................................... A61K 33/22
[52] U.S. Cl. .......................... 504/187; 504/122; 504/153; 504/164; 504/193; 71/31
[58] Field of Search ..................................... 504/187, 122, 504/153, 164, 193; 71/31

[56] References Cited

U.S. PATENT DOCUMENTS

| | | |
|---|---|---|
| 4,461,638 | 7/1984 | Rajadhyaksha .............................. 71/27 |
| 4,589,906 | 5/1986 | Brunn et al. ................................. 71/80 |
| 4,844,725 | 7/1989 | Malout et al. ................................ 71/3 |

*Primary Examiner*—Francisco Prats
*Attorney, Agent, or Firm*—Klaus J. Bach

[57] ABSTRACT

A method of treating plants to raise their resistance to viroids and to protect them from the effects of viroid infections by administering bioassimilable boron compounds to the plants.

4 Claims, No Drawings

METHOD OF TREATING VIROID INFECTIONS WITH BIOASSIMILABLE BORON COMPOUNDS

This is a Divisional appllication of Ser. No. 08/859,733 filed May 21, 1997, now abandoned, which is a continuation-in-part application of international appplication PCT/EP95/04494 filed Nov. 15, 1995 and claiming priority of German application P 44 41 483.8 filed Nov. 22, 1994.

BACKGROUND OF THE INVENTION

The invention relates to bioassimilable boron compounds for fighting subviral particles which cause subacute, degenerative, non-inflammatory diseases and which are known as viroids.

Viroids are infectious particles which autonomously replicate in adequate host cells. They represent the smallest form of life. With subviral dimensions of about 10×1 nanometers, the rod-shaped structures are smaller than the most primitive virus. They consist of an annular molecule of ribonucleic acid; 246 to 375 nucleotides are combined, in a single strand and covalently closed to a tertiary structure of high stability wherein ⅔ of the opposite bases are paired in a complimentary fashion. There are also forms with open chains, simple and polymeric forms. Viroids are not surrounded by their own viroid-specific protein envelope. Up to now, viroids could be isolated as particles only from the cells of higher plants, but infectious ribonucleic acid cells of the same type have been found in connection with certain diseases also in the cells of vertebrates.

Besides the absence of cellular structures, a property which they share with the viruses, these smallest parasites are characterized in that they do not code any proteins. They do not leave any fingerprint in the protein machinery of the invaded cell, and in this manner, escape the antiviral defense mechanism of the infected host organism, at least during the incubation period.

In plants, the viroids cause no active or passive resistance. They induce neither hyperergic reactions nor the production of antiviral proteins.

The incubation periods are longer than with virus infections by orders of magnitudes. With long lived plants, they may be many years, but high temperatures (tropical climates) result in dramatic reductions of the latent periods.

The most frequent symptoms of a viroid infection in plants are:

- growth stunts
- upsetting
- necrosis
- bearing of small fruits
- death of the plant.

The symptoms are qualitatively about the same for all types of plants and for all viroids which indicates a disturbance at a central location in the cell control of the host. Injected in mammals, the viroids do not cause an immune response, in contrast to the viruses as a whole, including plant viruses. They do not induce the production of interferon It does not lead to a serologic reaction. The pathogenicity of the viroids lays beyond the classical definition of the infectious diseases by Pasteur and Koch.

The immunogenous differences between the two types of pathogens have to do with the fact that viruses cause transcriptional diseases whereas viroids cause post transcriptional diseases.

Viruses primarily upset the synthesis of all proteins and encode instead their own virus proteins, which, in mammal organisms leads to an immediate immune response. Because of their relatively large size as particles and because of their protein and/or glycoprotein envelope, the classical viruses are the model for a potential antigen. Viral proteins are resented on the hista compatibility molecules of the class I (MCHI).

In contrast, viroids and viroid-analogous pathogens utilize exclusively the proteins of the hosts. This and their small size eliminate right from the start any presentation as antigen with the resulting immunogen reaction.

The metabolic damage effects of the viroids begins at a relatively late stage by post transcriptional disturbance of the protein and glycoprotein cycle of the host. Caused by the viroids, this may lead to:

- alienation of functions
- impediment of transmembrane transports
- blocking of disintegration
- protein polymorphism as a result of erroneous processing.

This leads to concentration accumulations of nontransferred, nonrecycled and, depending on the circumstances, processed host proteins in stagnating cellular or intercellular pools where, by crystallization, mineralization, fibrillization, and/or amyloid plaque formation, they become immune to attacks by proteinases and are irreversibly deposited. The viroid-caused malfunction of the body's proteins permits the immune system only to employ autoimmune antibodies and this only at a late stage after the disturbance has become irreversible, that is, in the final stage of the disease. In fact, in the late lethal stages of subacute diseases caused by viroid-like particles in animals, autoimmune antibodies were found which are directed against the crystallized proteins of the host. With mice, an influence of the histacompatibility genes of the class II(MHCII) on the course of the infection has been found. The sponge-like perforation of infected nerve tissue as a result of inflammation-free spontaneous cell destruction reminds of apoptotic autodestruction mechanisms of the cells like they can be initiated by autoimmune signaling. By their primitivness and their sequentially genomic proximity as well as their compatibility to functional host cell ribonucleic acids (intranen, 7S, 7SL-RNA's, ribonucleasis P and L) viroidal and assimilated infectious particles have eluded up to now any selective curative influence since each directed action against the viroid parasite affects negatively also essential host cell functions.

Of all parasites the viroids and other subviral molecules have the closest functional proximity to the components of the host cell, from which right away maximal difficulties with regard to their identification and their control can be expected.

Viroids of plant cells can be isolated as single structures and are visible in an electron microscope. Blot methods are highly sensitive and permit the determination of a single viroid per cell.

In the animal and human area however, it has not been possible so far to observe and isolate disease-specific viroid-analogue ribonucleic acids in free form as unpackaged autonomically operating particles, but they were found in infected tissues. Under the physiological conditions of the animal cell, ribonucleic acid (RNA) is packaged in protein at the strands forming during the transcription, the replication and the processing. Specific bond affinities to molecules of the host cell resist the existence of naked RNA-viroid particles. In addition, the body temperatures present in warm blooded beings favor the dissolution of eventually possible autonomous structures of animal viroids. At 38° C. also plant viroids are present in already molten modifications which are highly susceptible to associations.

The energies occurring with intermolecular associations are larger than those which can be obtained by the actuation of the still available intramolecular self complementary base airs (1,2 kcal/pair of nucleotides). The complexes are more stable than the viroid particle on its own. Viroid-like pathogens in animal cells are permanently in an ecliptic state. Their transmission by means of infected cell material does not require the formation of singly packaged visible particles as it is the case with viruses; this would be prevented already by the low coding capacity of such viroidal and other subviral RNA's.

Specific intermolecular bonds of subviral RNAs exist to host-cellular nucleonic acids (anti-sens-RNA-segments, anti-genomic bonds) to lipids (phospholipids) and to the enzymatic and physicochemical highly resistant fibrilous or amyloid pathogenic protein associates. The pathogens are packaged and masked. The association becomes biologically indestructible by reciprocal stabilization of its components.

Fibrilous and amyloid protein aggregates form stagnating pools presumably with the cooperation of the viroidal parasites. This leads among others to post-transcriptional point imitations of host-coded normally not pathogenic proteins; In certain positions hydrophilic amino acids are substituted by lipophilic and acidic ones by basic amino acids. The bundled pathogenic, highly resistant, prion-protein aggregates are believed by some authors to have the capability to replicate.

In parallel therewith, the afflicted neurons have an increased affinity to basic microscopic coloring agents (basophilic character).

A strong lipophilic affinity of the pathogens or their associations contributes to their capability to undermine defense reactions from the aqueous serological environment. The shifting to the lipophilic environment is also apparent from the preference of the pathogens for lipid-rich tissue in the invaded host: the brain, the nerve strings, the spinal cord, the hypophysis, the spleen, the eyes, the lymphocytes, the intestinal tract and all secretarial tissues are main target organs.

Pathogens in such infectious tissues can be inactivated by treatment with lipophilic solvents (acetone). Plaques and fibrils of the prion-proteins can be dissolved by subsequent exposure to nucleases and proteinase K.

While the replication cycle of the viroids in plant cells is known, the activity of viroid-like particles in the animal and human areas is not yet understood.

It is known, however, that all types of viroids are highly infectious and that the viroidal particles are quasi-indestructible. In contrast to bacteria and viruses, it is practically impossible to eliminate them from a contaminated environment and this leads to a cumulative biocontamination.

For this reason, it is economically highly important that viroid infections in the plant and animal area can be controlled without destructive side effects.

In the plant environment, viroid infections lead to enormous damage over large areas, particularly in tropical climate zones. Wild and cultured plants are equally affected in those areas.

The coconut Cadang cadang Viroid (CCCVd) has destroyed already 30 million coco palm trees (Cocus nucifera). The ultra small particles of 10 nm cause 20 m high tree giants to die, 800,000 per year in the Philippines. The destruction in herd-like expanding zones is so complete and the transmission of the viroids so unavoidable and prompt, that extinction of the respective species and of the viroid-tolerant related species must be feared.

In moderate climate areas, selective monocultures and green house plants have experienced heavy viroid epidemics, particularly high performance species which were grown for particular properties. Wild plants barely develop symptoms, but they provide a permanent reservoir for new epidemics in the cultured plants.

One of the most virulent viroids in our climate zone is the spindle tuber viroid (PSTVd) of the potatoes. It is polyvalent and attacks a large number of cultured plants. With 356 to 360 ribonucleotides, it belongs to the large viroids (The upper existence limit for the viroids known so far is about 375 ribonucleotides).

Large viroids such as PSTVd have a large host circle. Small viroids such as the above mentioned CCCVd (246 ribonucleotides) attack only one or a few related species. In this connection, it is to be pointed out that the known viroids are not evenly distributed over the narrow range of existence between 246 and 375 ribonucleotides, but that they are present in a cumulative manner: At the upper and lower limits and in between at distances of about 20 nucleotides, there is an accumulation of the various viroid types. The nucleic numbers in between are unoccupied.

PSVTd can occur in isolates with mild, strong or lethal symptom development. Field potato cultures infected with strong isolates suffer yield losses in warm summers of 60% (growth delay, small fruits). Greenhouse plants are even more susceptible. A virulent PSTVd strain can eliminate greenhouse plants 100%.

In the animal and human area viroid-like particles and viroid segments integrated in viral genomes are suspected to be responsible for a number of degenerative non- or post inflammatory diseases of the central nervous system. After long incubation periods and latent periods, they can lead to grave neuropathologic disturbances and then always to death.

Viroid-like parasites are believed to be responsible in mammals and in humans solely or as a cofactor for about 50 subacute chronic illnesses. They are listed in the following 5 groups in the order of lower confirmation of the knowledge concerning the viroid participation:

1. Virosoids are well defined partially sequenced particles which contain a non-coding viroid component and which become infectious with the aid of a helper virus. They occur in plants (satellite viruses, multiparticle viral genomes) and in animals.
2. Non-conventional Lenti-viruses represent an extensive still little defined group. Included therein are the pathogens of degenerative diseases of the central nervous system which always result in death after the symptoms appear; they have the above mentioned pathological and histochemical effects: spongelike perforation of the brain and nerve tissues by the death of nerve cells, formation of fibrilious and amyloidal protein aggregates by erroneous processing of genetic products, astrocytosis (hypertrophy of the astrocytes under formation of acid, fibrilious glycoproteins), behavioral disorders, progressive pathogenesis of numerous organs. The group of spongiform encephalitis includes: Scrapie diseases of sheep (for example, 18000 cases in one immunization accident in the UK) cattle madness (Bovine spongiform encephalitis=BSE, 10000 cases annually in GB) and, in humans, the Creutzfeldt-Jakob disease(CTE), the Gerstmann-Straussler syndrome (GSS), the Kuru-and the Alper's disease. The pathogens overcome the species barrier and are potentially infectious to all mammals.

The importance of the non-conventional viruses is increased by the suspicion that they are co-responsible for a long list of other chronic diseases; Alzheimer's dementia (clinically not distinguishable from a slow CTE, 800,000 potential cases in Germany which occur at increasingly younger ages), the Parkinson's disease, numerous autoimmune diseases, sclerosis, for example, lateral sclerosis, epilepsies, schizophrenias, endogene depressions, behavior anomalies and the Autism.

3. Homologies of the viroids with retroviruses and cell transforming DNA viruses.

Retroviruses and viroids have a number of common properties: Classic viruses cause inflammatory processes, viroids cause degenerative processes. Retroviruses combine both properties and functionally bridge the difference between the classical viruses and the viroids.

Viroids, on the other hand, have retroviral properties. Because of their ability to become an integral part of a genome and again to splice out therefrom, they are, on an RNA basis, the functional equivalent of the retroviral proviruses in the DNA genome with whose long terminal repeats (LTR), there are sequence homologies. Such noncoding sequencing repetitions play a role in the translation or retranslation of viral information between RNA and DNA. Highly conserved viroid sequences, which are present in all viroids, appear to be active also in retroviral genomes.

There are analogies also for the replication cycle: Retroviruses and viroids use the same cellular enzymes: DNA-dependent RNA polymerases.

A controlled modification of the pathogenic properties of the relatively simple viroids may contribute to a better understanding of the role of the LTR in the much more complex retroviruses and to a controlling influence on the latter.

Furthermore, the genomes of the DNA viruses of the families Parvor, Hepadena, Polyoma, Adeno and Herpeto also have sequence repetitions which contain the typically conserved viroid sequences as basic building block. With their multiply repetitious "Rolling Circle" mechanism, the viroids are the base model for the formation and functioning of noncoding sequence repetitions on the basis of RNA and DNA.

Generally, it seems that conserved viroid sequences (for example, the central palindromic deka nucleotides of the viroids) are necessary for the interaction of the viroids between the active replication phase and the occasional disappearance in the DNA genome of a host which shows no symptoms during that period.

4. Subacutely persisting classical viruses. A number of degenerative diseases is caused by classical RNA viruses. After subsidence of the main infection, viral subspecies survive the immune defense in a defective condition with altered antigen pattern; they persist in the nerve strands and move there, similar to the Lyssa-viruses (rabies), from cell to cell. After, at times, very long latent periods, they cause grave, generally deadly neuropathological late follow-up diseases (measles, rubella, polio, or multiple sclerosis, the multiple sclerosis as a late follow up infection of non permissive human cells by Theilers Murines polio viruses).

A viroids participation in these late follow-up infections is under discussion for two reasons:

1) Viroids are highly complex double strand RNAs. Such segments serve, on one hand, as induction signals for the production of interferon which may result in the more or less complete neutralization of conventional viruses during the acute initial infection stage. If this mechanism does not work perfectly, classical viruses remain, leading potentially to late follow-up infections.

On the other hand, double strand RNA segments act as pivots for the stabilization of RNA virus genomes and, in this manner, are responsible for the distribution width of the quasi-species population and the amount of the defective subspecies formed. The more remote such defective subspecies are from the initial antigen specimen, the better are their chances for survival.

5. Viroid participation on genetic diseases. In the area of plants, the egg cell is the main aim and most important vector of a viroidal infection. In analogy therewith, vertical viroid transmission with chromosomal damages to the egg cell cannot be excluded in the animal area. For genetic diseases which depend on the maternal part and which, and consequently correlate with the conception age thereof (for example Down Syndrome), a viroid participation in initiating the chromosome anomaly is well possible. An indication herefor is the brain amyloidosis, which may occur during the trisomy disease proceedings and which is otherwise characteristic for nonconventional, atypical "Slow Virus" diseases.

Viroids and assimilated infectious particles have an unusual physical, chemical and biological resistance.

The inactivation by UV, ionizing and neutron irradiation, by heat, formaldehyde and alcohol and by nucleases and proteins is effective only in a limited manner.

The potato Spindle Tuber viroid is 20× more resistant against UV irradiation than the most stable viruses, Scrapie-Agens are even 200× more resistant. The latter is also resistant to stomach acidity and temperatures of 350° C. Land grazed on by Scrapie-infected sheep remains infectious for some years. The failure of the classical decontamination and disinfecting methods have been demonstrated in the human and animal medicine areas by spectacular accidents.

Viroids from diseased culture plants deposit themselves in wild plants as latent viroids or trace viroids, without causing any symptoms and they wait there for adequate hosts. They establish themselves firmly in a practical biological living area and survive the changes thereof.

By industrial farming with large area use of cultivating and cutting machinery, the active and latent viroid reservoirs are regularly and massively mixed. The vector density and velocity of the viroid transmission are therefore very high. Multiinfections (viroids, plant viruses) occur more and more frequently. No adequate defense mechanisms exist for this situation introduced by industrialization in contrast to the normal evolution and in an abrupt manner. The results are a large area destruction of sensitive (viroid tolerant) vegetation species and a cumulative bio contamination of the plant life by more and more viroid types and strains.

Also in the animal raising and human areas, the risk factors for a systematic transfection of the population by the pathogens of the subacute encephalopathies which came in contact with viroid like RNA molecules are increasing.

Keeping animals in large numbers under industrial conditions and the recirculation of waste from meat processing plants for the purpose of feeding have lead, among all breeding and domestic animals, to an expansion of Scrapie, cattle madness BSE and its variants. Among the same type of animals living in the wild, such epidemics are not known. At least sporadic infections pass without symptoms. If the same animals are subjected to the same conditions as domestic animals or if they are contained in ecological gardens, they also become ill.

The various pathogens overcome the species barrier between the mammals more or less easily, possibly by way of an intermediate host as they may be without symptoms for some time, like the plant viroids. Series paths in the new host then shorten the incubation periods and increase the virulence, The use, since 1981, of ground feed of Scrapie infected sheep led in England in 1987 to an outbreak of cattle madness (BSE) which was unknown before, but is epidemic in England today and has worldwide sporadic outbreaks. All livestock and all domestic animals can be infected. Industrial growing methods, immunization and doping guns are potential causes for spreading infections.

It appears that for the various pathogen isolates, there is a correlation between the ease with which they overcome the species barrier and adapt to a new host and effectiveness with which they extinguish the infected individuals of the infected population: The not very easily adaptable species-stable Scrapie pathogen of the sheep cannot be easily transferred to other animal species, but completely destroys its host species, the infected sheep herd. On the other hand, the bovine BSE pathogen, which easily switches from one to another species, leads to fatalities in only a few individuals of the infected cattle herd. That means that, in a relatively unspecific pathogen strain (with a wide host spectrum), the infected individual has a better chance to delay or avoid development of lethal symptoms.

In order to estimate the potential risk for humans, man must also be considered to be a mammal living in a concentrated life style.

A transfer between animal and human, for example by contaminated live stock and domestic animals, has occurred epidemiologically by Scrapie (sheep) Creutzfeldt-Jakob-Encephalopathy (human) and it has been experimentally shown that humans can be a vector and infect animals. The earlier described target organs of the pathogens were particularly infectious: The nerves, lipid and secretarial tissues, (the sale of which is no longer permitted in France if they originate from cattle or eggs). But also muscle tissue and milk products can not be excluded from the contamination chain.

The human to human transfer of the spongiform encephalopathies in the area of medicine has been proved by dramatic special cases. The epidemic extent cannot yet be judged, because the pathogen appeared only recently and the incubation period is so long. Preventative measures are hindered by:

- the quasi indestructibility of the pathogens (classical hygiene and enzyme treatments are ineffective).
- The universal transmission routes (The importance of the transmission method is limited to influencing the duration of the symptom-free latent period: for example, massive seral inoculation close to the brain have the fastest results as it has been described for rabies whereas small amounts of infectious material administered orally resulted in extremely long incubation periods).
- non-existence of adequate safety tests (the death of the patient is the sole criterium).

A post infectional treatment has not been known so far either.

With the present state of the art, a potential risk of a transmission is present:

- during surgical and dental treatments (surgical instruments, implants, electrodes) in dental nerves concentrated pathogens for example have led to the contamination of dentists and their patients.
- with all organs, tissue and bone marrow transplants. Particularly risky are organs after a certain time after the death of the donor when they are aged but still usable such as cornea, dura mater; the virulency stimulation of the pathogens is believed to be the cause by producing an increased amount of stress protein in the dying donor organisms. This means that the later the contaminated tissue is taken from the dying donor, the more infectious it is.
- with transfusions and serum products (a safe sterilization or decontamination of the products is impossible because of the small size and the high resistance of the pathogens).
- with extracts from human and animal organisms (hormones, interferon), the use of growth hormones of hypophyses of dead donors for example has led to the contamination of all the children age 4 to 16 treated with a particular sample.
- a risk exists also for all pharmaceutical strengthening and regeneration preparations which contain extracts of lipidrich animal organs.

Consequently, all the negative conditions for a cumulative bio-contamination by viroids of the higher plants as well as of the higher animals by viroid-like particles are in place.

The fight of the smallest against the largest occurs in the metabolism with minimal differences. The lack of information and incapability of coding of the pathogens have the effect that they proliferate exclusively on the basis of host factors. With their expansions across individuals and across species, the virulence of the viroid pathogens increases (in contrast to viruses where the species transfer may result in less virulent viruses).

The industrialization of the nature increases the susceptibility of the hosts: Particularly overbred animals and plants grown in large quantities and in monocultures are highly susceptible.

As a result, isolated mutations and statistically rare cases of faulty processing of genetic products, which may occur sporadically in individuals could lead to a global pandemic whereas, with the undercritical conditions existent in the pre-ndustrial society, they would have been limited to island-like areas and would have self-destructed.

A miniature model for a global ecological problem situation of the "slow virus" epidemic is the Kuru disease in New Guinea which can safely be traced to a sporadic case of Creutzfeld-Jakob (CJE) of a Papua aborigin. The ritual buryial cannibalism became the vector of the Kuru epidemic which extended also to uninvolved small children who were contaminated only by accidental contact with the infectious tissue. In 1957, the buryial ritual was no longer permitted by law. This eliminated the main vector. As a result, the epidemic subsided. Especially, no children born afterwards became sick. But even today, Papuan adults anywhere in the world may die as a result of a participation in a buryial ritual that happened more than 30 years earlier.

Altogether in a number of years, a sum of risk factors became apparent; dangerous, infectious, highly resistant, ubiquitary, ultra small pathogens with extremely long incubation periods and metabolic minimum differences from host factors are contrasted by less and less resistant host organisms.

In the animal and human areas, it is further to be considered that the pathogens are undetectable, that is, they are transmitted in various ways, that there are no adequate tests and that there are no specific disease symptoms so that a certain diagnosis can be obtained only after death.

An antidote must be capable of distinguishing in a highly specific manner between the normal and the quasi-identical pathogenic molecules on both sides, the host and the pathogenic side and must be able to selectively affect the latter ones in an inhibitory manner.

Such an antidote against viroids and viroid-like pathogens has not been known so far with the exception of cell poisons.

It is the object of the invention to show a new use of boron compounds which can be bio-assimilated.

SUMMARY OF THE INVENTION

In a treatment for fighting off subviral particles which cause subacute degenerative non-inflammatory infectious diseases of the central nervous system in animals and humans or for the protection from the effects of subviral pathgens in plants, a medication including bioassimilable boron compounds is used.

The use of boron compounds in accordance with the invention is advantageous for the protection of plants: wild, garden, greenhouse cultures, tree and plant growth with regard to pathogen viroid infections, wherein bioassimilable inorganic or organic boron compounds are supplied to the plants in the soil or by other nutrient procedures within the tolerance limits of a particular species or type and wherein the application form may be any type of soil, plant and generally biocompatible inorganic or organic boron compound or mixture thereof, preferably an aqueous solution of boric acid, of borates which are neutralized if necessary, of organic boron compounds, particularly of boratechelatin complexes with polyoles such as glycol, glycerin, mamitol or sorbitol, with oxycarbonic acid such as milk, wine or citric acid or in the form of carbohydrate complexes with glucose, galactose, fructose, maltose, lactose or any other type of mono-, di-, oligo-saccharides as glycosidic ligands.

The application of the boron containing solutions can be done by nutrition via the soil or via hydroculture or via the leaves by spraying or in both ways. For soils, the preferred application is by neutralized borates, for hydrocultures and for the application via the leaves, borate complexes with polyhydroxy compounds are preferred.

For the tomato type Rentita, advantageous dosages are a permanent content of 1 ppm boron in a nutrition solution and for peat soil cultures, regular watering with solutions of 2–5 ppm boron in amounts which result in a total boron supply of 2–5 kg boron/ha. They will bring about a 10 to 15 times enrichment with boron (100–150 ppm) as compared with untreated plants (10–15 ppm) and at the same time, increased growth.

Considering the dosages of boron in soils, it is advantageous to take into consideration the adsorption and desorption properties for the respective boron compounds and to determine them if necessary in advance in accordance with the classic methods.

The upper tolerance limit for boron is moved to substantially higher concentration ranges when simultaneously bioavailable silicon is applied whereby the plant growth is further increased. In tomatoes this results in in a boron enrichment by 20–30 times of theie natural boron content if the hydroculture nutrient solution for example contains 1–2 ppm B and 100 ppm Si in the form of neutralized water glass.

If industrially available forms of soluble silicates such as blast furnace slag are used, other trace compounds such as manganese contained therein should be predetermined and their effects on the plant/soil/viroid system should be taken into consideration.

Non-pathogenic inoffensive viroid strains which are grown, by manipulation, in highly boron enriched plants have a high proliferation capability, that is, they are highly infectious but not toxic.

The use of such non-pathogenic boron-modified viroid strains, for example, in the form of infected cell material, for the preventative inoculation of endangered cultures serving as protection from infections by related viroid strains of high pathogenicity leads, by utilization of incompatibility phenomena, to a state in which the first infecting, cell occupying viroid inhibits the development of subsequent related viroids.

When utilizing extracts of all kinds of boron-enriched plants, it is preferred to use plant strains which have a relatively high boron accumulation already in their natural environment such as crocus sativas (up to 5000 ppm boron) or the poppy varieties (300–1000 ppm boron). Extracts of all types of plants growing on naturally boron-containing soils (high geogenic boron concentration of the soil) are also advantageous.

If extracts are used, whose compatibility has been improved for example by the removal of toxic alkaloid compounds and other undesirable accompanying compounds, the daily doses can, if tolerated, be increased to an equivalent of 5 mg boron/kg mammal weight and, after a certain adaptation period, to even more.

In addition to this therapeutic administration, boron-enriched and naturally boron-rich mineral water may be used.

Toxic effects by accidentally exceeding the individual boron tolerance limits can be neutralized by administering copper compounds and to some extent magnesium and calcium which act as antidotes.

Viroid-analog infectious agents which may develop in the infected cell material by the boron manipulation have little or no pathogenicity for the host organism.

The use of slightly or non pathogenic subviral agents obtained by such boron manipulation results in a protection of uninfected tissues and organs in organisms infected by lethal pathogen strains, wherein this protection is the result of incompatibility phenomena, not of a classic immune system activation (inoculation response).

Below the invention is explained in greater detail on the basis of some examples.

It has been found that, surprisingly, a treatment of plants and cultures with inorganic or organic boron compounds that can be bio-assimilated, the symptoms of the viroid infection can be suppressed. This has been found in the example of the experimental system "Potato Spindle Viroid" (lethal strain KF 440/2)/tomato(type Rentita). The boron-pretreated plants escape the destructive effects of the viroid infection without exception and, with a permanent and sufficient supply of for example boric acid or neutralized borox, live through a normal life and reproduction cycle. They actually produce more biomass and fruits than non-infected control plants which are grown otherwise under the same conditions, whereas infected but not pretreated plants die without exception.

The supply of boron can occur by nutrition through the nutrients or in the soil and/or by application to the foliage. The treatment can be preventative or curative. Protection before the infection is most effective. Protection after infection, particularly the application of boron compounds to the foliage, protect those areas of the plant which are still free of symptoms and prevent them from dying but damages which have been fixed already morphologically (loss of growth, necroses, bearing of small fruits) cannot be corrected.

Some of the plants were enriched also with bioassimilable silicon (neutralized waterglass). This experiment showed that the silicon extended the normally narrow boron tolerance limits: the toxic effect of the boron compounds is moved to substantially higher concentration ranges. Plant-available silicon has, so to say, the effect of an antidote against the herbicidal effects of larger amounts of boron compounds.

It is noted that, unlike all the other tested trace elements, silicon alone without the application of boron does not stimulate the virulence of the viroid infection and does not accelerate the dying of the plants.

To insure the effects achieved with the present invention and for further delineation with regard to the state of the art a number of additional experiments were performed. It had to be confirmed that it was a selective effect, which was not he result of an unspecified general increase of the natural resistance of the plant by a sufficient offer of the needed trace element boron.

1. This is indicated by the fact that other trace elements tested so far (for example, manganese, silicon) which, as is well known, also improve growth and resistance of the plant, have effects in the opposite direction, that is they increase the pathogenic effects of the viroids; only boron provides, selectively, the described protection.

2. The fact that boron-protected infected plants cause the production of more biomass than control plants which are only enriched with boron but not infected by viroids, indicates that something is happening which cannot be obtained additively from the earlier state of the art. Since the infected plant first has to provide the synthesis efforts for up to 20000 viroid particles per cell and then has to suffer their pathogenic effects, its biomass production should, on the basis of the state of the art knowledge, in any case be substantially lower than that of the uninfected control plants.

3. The dosage of the viroid particles in the infected plant material by molecular hybridization and Northern Blot resulted for the boron protected plants surprisingly in a 5 times higher viroid concentration than in the control plants with the normal boron content: The viroid is still present in the cells of the boron protected plants and furthermore in higher concentration, but it has become inoffensive to the plant.

Consequently, the protective effects are not the result of a simple nutritive strengthening of the defensive forces against viroid replication already present in the plant, but of a modification of the pathogenic properties of the para sites. In this connection, a distinction has to be made between infectiosity (number of infectious particles) which increases and the pathogenicity (extent of cell destruction) which is being neutralized. Boron compounds cause the formation of nonpathogenic viroid strains which possibly even have support functions in the host cell metabolism (more biomass) what could be taken as an indication for the reason and development of the viroids. Under the very likely condition that, by evolution, viroids originate from cell-characteristic RNA which went out of control, the effects of boron would indicate a reversal of the degenerative process, that is a retransformation of viral RNA segments toward the normal constructive cellular functions.

4. It was further to be shown that the boron compounds offered to the plant are indeed localized in the infection susceptive or infected leaf material at the location of the viroid replications. Spectroscopic measurements (AA/ICP) have shown that the leaf material of the boron treated plants have 10 times the boron content (100 ppm) as compared to normal tomato plants. This amount is doubled by concurrent addition of silica. Within the already boron enriched cell mass, the boron has a greater concentration at the place of the viroid synthesis, that is, within the cell core and in the nucleolus, there is selectively on increased concentration. A major amount of the boron supplied to the treated plant is, consequently, in direct contact with the nascent viroid molecule.

5. As the simplest model of a pathogen, the viroid comprises only a small molecule ribonucleic acid. The changes of the infectiousness and the pathogenicity by the effects of the boron compounds must be represented in the primary and secondary structures of this sole pathogen molecule and it should be possible to make them visible by physical or chemical means. NMR measurements show that boric acid forms specifically a bi-complex with the ribonucleotide GMP and is capable of bringing free and 5-terminal GMP molecules selectively together thereby engaging directly in the processing of the viroids being generated. With its particular tendency to fill the empty $p_z$-orbital under formation of a $sp^3$-tetraeder structure, boron exerts a specific affinity to nucleophilic ligands and is in a position, to strongly selectively influence quasi-identical viroid molecules and the pertinent host factors.

In this connection, boron appears to cause the formation of thermodynamically stable viroid base bodies with little tendency to forming loops and a greatly delayed behavior (=intramolecular release). Stable viroid modifications melt only at higher temperatures. For its pathogenicity to become effective and for obtaining a wide host spectrum the viroid molecule would need tertiary structures which are present already at the temperature prevailing during the infection and which easily and rapidly form a large number of loops and branches, which facilitate the specific attachment to factors of the host cell. The favoring by the boron of stable viroid strains with difficult melting behavior explains at, least partially, its antipathogenic effects on viroids.

The invention further resides in an extension of the method by means of boron compounds, of combating the patho- genicity of viroid-analogous infectious RNAs and other subviral molecules in animal and human organisms where they are participating as initiators for the above described subacute degenerative diseases of the central nervous system possibly together with cofactors of cell endogenic or exogenic origin.

Because of the long reaction periods and the particularly difficult experimental conditions, the effect of boron compounds is supported here mainly in an epidemiological manner and further prove is provided by analogous conclusions taken from viroid infections in plants and from the physiological behavior of the boron compounds in the animal cell.

It is also noted that, with the now worldwide spreading of the spongiform encephalopathies Scrapie (sheep) and BSE (cattle), certain geographic regions are spared. These are regions which, in earlier epidemiological studies have caught attention by their quasi-absence of animal and human tuberculosis types (mycobacterium tuberculosis and M. Bovis) and which have an extremely high natural boron content in their soils, for example, the boraciferous volcanic regions of Italy and parts of northwest Kasachstan and of the Atlas mountains. The plant species growing there have developed, with their boron containing soils, a formidable tolerance for boron and have boron contents which would be toxic for the same plant species growing at a normal location. The high boron contents are transferred, by the food chain, to the animal world and, after a certain adaptation period, is tolerated by the individuals living there. The permanent ingestion of the boron-enriched plant parts provides in animals for protection from infection, that is, from an appearance of any symptoms.

Animals brought into boraciferous regions will generally readily adapt to the high boron content of their biotops; at times an adaptation period is needed. Only a small percentage of individuals develop symptoms of boron toxicity. With sheep, these symptoms are similar to the symptoms of the Scrapie disease but, in contrast to the disease, they are reversible if the boron stress is removed. Boron-toxic effects can be fixed for animals by giving them copper-, magnesium-, and calcium compounds. The acquired boron tolerance remains genetically fixed.

As a further support for the belief that the concept of combating viroid infections by boron compounds can be transferred from plants to animals, it is noted that it has been found that the eczema-like Prinugos (itching plait) which is characteristic for the Scrapie disease can be treated successfully by local application of boron compounds (for example, boroglycerin—solution). This is the only example of a partial remission, although temporary, of the otherwise merciless progress of the infection to the death.

A further indication is the cell physiological behavior of the boron compounds. In the plant and animal metamorphy, boron is the most diffusion active element. Borates and their derivatives penetrate with high speed cells, cell compartments and organelles, hydrophilic and lipophilic zones, organs and organ barriers (for example, the placenta barrier; the heart fiber membranes, in pathological situations even the blood-brain-barrier opens up). Similar to the pathogens, the boron compounds exert an influence on the permeability of the mem branes by separating the phospholipid structures. Boron is enriched or its concentration is decreased depending on membrane specific criteria.

In the infected animal and human organism, the about equally distributed small boron amounts (0.5 ppm) are mobilized and are transported to the places of the necrotic cell destruction which is an indication that boron plays a pivotal role in the fight for survival that is the apoptetic selfdestruction of the infected cells.

Because of the absence of a suitable radio isotopes the pivotal role of the boron in the spontaneous cell degeneration by autophagic processes has not been recognized so far.

Because of the suction effect which the infected pathogenic zones of an organism have with respect to the naturally available or therapeutically applied boron, its role at the location of the infection is kinetically favored. Like in the infected plant, the pathogen as well as the boron are concentrated in the same areas also in the animal organism and there, they come in optimal contact with each other.

Like in the plant, the boron supplied to the animal and human organism is selectively concentrated in zones of increased metabolic activity that is at any place where bio-masses are rapidly generated or degenerated, particularly in cells infected by viral or subviral pathogens in tumor cells, particular in nerve and cerebral tissues in areas of necrotic cell destruction (spongiform perfora tion in the brain, necrotic infarcted areas in organs)

at the beginning of a pregnancy in the fetus.

A further indication that non-conventional disease pathogens and boron compounds are active specifically at the same cellular interconnect locations is the fact that the human toxic effect of high-excess boric acid and the pathogenic effect of the subviral pathogens to be combated generate an almost identical clinical picture: headache, depression, convulsion, hyperasthesia, tremors, rigor, akinesis, ataxy, meningitis, deliria, and sensual deception which may be accompanied externally by eczema formations.

What is claimed is:

1. A method of treating plants infected with viroids to raise their resistance to viroids and to protect them from the effects of subviral infections by administering bioassimilable boron compounds to plants infected with viroids in an amount to provide in the plants a boron concentration of 100–150 ppm.

2. A method according to claim 1, wherein the dosage of said boron administrations is selected in accordance with the plant species to be protected.

3. A method according to claim 2, wherein each plant species has an upper tolerance limit for boron compounds and boron compounds are administered up to said upper tolerance limit.

4. A method according to claim 3, wherein said upper tolerance limit for boron compounds is raised to increased concentration ranges by concurrent administering of bioavailable silicon.

* * * * *